US009955950B2

(12) United States Patent
Kulakowski, Jr. et al.

(10) Patent No.: US 9,955,950 B2
(45) Date of Patent: May 1, 2018

(54) SYSTEMS AND METHODS FOR STEERING MULTIPLE ULTRASOUND BEAMS

(71) Applicant: General Electric Company, Schenectady, NY (US)

(72) Inventors: Richard Marion Kulakowski, Jr., Wauwatosa, WI (US); Michael Charles Macdonald, Wauwatosa, WI (US); Justin Daniel Lanning, Wauwatosa, WI (US); Michael Wang, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 506 days.

(21) Appl. No.: 14/447,110

(22) Filed: Jul. 30, 2014

(65) Prior Publication Data
US 2016/0030005 A1    Feb. 4, 2016

(51) Int. Cl.
*A61B 8/00* (2006.01)
*A61B 8/08* (2006.01)
(Continued)

(52) U.S. Cl.
CPC .............. *A61B 8/485* (2013.01); *A61B 8/14* (2013.01); *A61B 8/4444* (2013.01);
(Continued)

(58) Field of Classification Search
CPC ..... A61B 8/485; A61B 8/4444; A61B 8/4488; A61B 8/4483; A61B 8/4455; A61B 8/54;
(Continued)

(56) References Cited

U.S. PATENT DOCUMENTS

| 5,261,408 A | 11/1993 | Maslak et al. |
| 5,447,158 A * | 9/1995 | Nakajima ............... A61B 8/06 600/455 |

(Continued)

FOREIGN PATENT DOCUMENTS

| EP | 0414261 A2 | 2/1991 |
| WO | 01/90776 A2 | 11/2011 |

(Continued)

OTHER PUBLICATIONS

"Comb-Push Ultrasound Shear Elastography (CUSE): A Novel Method for Two-Dmensional Shear Elasticity Imaging of Soft Tissues," Song. et al., IEEE Transactions on Medical Imaging, vol. 31, No. 9, pp. 1821-1832 (Sep. 2012).

(Continued)

*Primary Examiner* — Sanjay Cattungal
(74) *Attorney, Agent, or Firm* — Dean D. Small; The Small Patent Law Group, LLC

(57) ABSTRACT

An ultrasound system may include a curved probe having a first set of elements that define a first aperture, and a second set of elements that define a second aperture. The probe may be configured to simultaneously transmit first and second ultrasound signals from the first and second apertures, respectively. The first ultrasound signal is configured to be transmitted in a first direction that is parallel with a first beam axis of the first ultrasound signal. The second ultrasound signal is configured to be transmitted in a second direction that is parallel with a second beam axis of the second ultrasound signal. At least one processor is configured to independently steer each of the first and second ultrasound signals.

41 Claims, 10 Drawing Sheets

(51) Int. Cl.
*A61B 8/14* (2006.01)
*G01S 15/89* (2006.01)
*G01S 7/52* (2006.01)

(52) U.S. Cl.
CPC .......... *A61B 8/4455* (2013.01); *A61B 8/4483* (2013.01); *A61B 8/4488* (2013.01); *A61B 8/54* (2013.01); *G01S 7/52042* (2013.01); *G01S 15/892* (2013.01); *G01S 15/8927* (2013.01); *A61B 8/4405* (2013.01); *A61B 8/4427* (2013.01); *A61B 8/467* (2013.01); *G01S 7/52084* (2013.01)

(58) Field of Classification Search
CPC ......... A61B 8/14; A61B 8/467; A61B 8/4405; A61B 8/4427; G01S 15/8927; G01S 7/52042; G01S 15/892; G01S 7/52084
USPC ................................................ 600/437–469
See application file for complete search history.

(56) References Cited

U.S. PATENT DOCUMENTS

| | | | | |
|---|---|---|---|---|
| 6,248,073 | B1* | 6/2001 | Gilbert | A61B 8/56 600/443 |
| 6,423,004 | B1 | 7/2002 | Dong | |
| 8,753,277 | B2 | 6/2014 | McAleavey | |
| 2004/0147841 | A1* | 7/2004 | McLaughlin | G01N 29/14 600/437 |
| 2008/0208061 | A1* | 8/2008 | Halmann | A61B 8/13 600/459 |
| 2008/0221454 | A1* | 9/2008 | Davidsen | G01S 7/5208 600/459 |
| 2008/0300490 | A1* | 12/2008 | Chiang | A61B 8/4236 600/459 |
| 2011/0046486 | A1* | 2/2011 | Shin | G01S 7/52085 600/443 |
| 2011/0054323 | A1* | 3/2011 | Ahn | G01S 7/52034 600/443 |
| 2012/0143063 | A1* | 6/2012 | Robinson | A61B 8/00 600/472 |
| 2012/0150036 | A1* | 6/2012 | Buckton | A61B 8/145 600/443 |
| 2014/0155738 | A1* | 6/2014 | Cheny | A61B 8/0841 600/424 |

FOREIGN PATENT DOCUMENTS

| | | |
|---|---|---|
| WO | 2012/116364 A1 | 8/2012 |
| WO | 2014/055973 A1 | 4/2014 |

OTHER PUBLICATIONS

International Search Report and Written Opinion regarding International Application No. PCT/US2015/042258, dated Oct. 6, 2015, 11 pages.

* cited by examiner

SYSTEMS AND METHODS FOR STEERING MULTIPLE ULTRASOUND BEAMS

BACKGROUND OF THE DISCLOSURE

Embodiments of the present disclosure generally relate to ultrasound imaging systems, and more particularly to systems and methods for steering multiple ultrasound signals generated by an ultrasound imaging system.

Ultrasound elasticity imaging is an elastography imaging modality that employs ultrasound waves to probe the mechanical properties of biological tissues and produce corresponding images. Shear wave elastography imaging (SWEI) is a type of ultrasound elasticity imaging. SWEI is based on applying acoustically generated shear waves to determine mechanical properties of the tissue, usually measured as a velocity, by tracking the displacement of the tissue at a plurality of points caused by the shear wave over time. The velocity relates to one or more mechanical properties of the tissue and may provide stiffness information measured in, for example, kilo Pascals (kPa). For example, a normal glandular measured from a patient is approximately 57 kPa, alternatively, a ductal tumor or breast cancer is approximately 301 kPa.

Many SWEI systems utilize a curved transducer that is configured to transmit multiple ultrasound push pulses into tissue of a patient. Typically, each ultrasound push pulse is transmitted in a direction that is normal to the face of the transducer. As such, the ultrasound push pulses diverge from one another, as the push pulses radiate outward from a curved face of the transducer. Each ultrasound push pulse may generate a shear wave in the tissue of the patient. Because the ultrasound push pulses diverge from one another, the distance between the origins of the generated shear waves may be relatively long. Therefore, the shear wave energy directed into the tissue, and therefore the tissue motion detected, may attenuate with increased depth.

BRIEF DESCRIPTION OF THE DISCLOSURE

Certain embodiments of the present disclosure provide an ultrasound system that may include a probe (such as a curved ultrasound probe or transducer) having a first set of elements that define a first aperture, and a second set of elements that define a second aperture. The probe is configured to transmit first and second ultrasound signals from the first and second apertures, respectively. Both the first and second ultrasound signals may be simultaneously transmitted. The first and second ultrasound signals may be ultrasound push pulses configured to generate shear waves in patient tissue, for example. The first ultrasound signal is configured to be transmitted in a first direction that is parallel with a first beam axis of the first ultrasound signal. The second ultrasound signal is configured to be transmitted in a second direction that is parallel with a second beam axis of the second ultrasound signal.

At least one processor is configured to independently steer each of the first and second ultrasound signals. For example, the processor(s) may be configured to steer each of the first and second ultrasound signals in relation to a central longitudinal axis of a transmitting component, such as an array of ultrasound elements, of the probe. In at least one embodiment, the processor(s) may be configured to steer each of the first and second ultrasound signals so that the first and second beam axes are parallel with the central longitudinal axis. The first direction may not be normal to a first face of the first aperture, and the second direction may not be normal to a second face of the second aperture.

In at least one embodiment, the processor(s) may be configured to steer the first and second ultrasound signals with respect to one another so that the first and second beam axes are parallel. For example, the processor(s) may be configured to steer the first and second ultrasound signal towards one another so that they are parallel with each other and the central longitudinal axis. The processor(s) may be configured to steer the first and second ultrasound signals to be substantially uniform with respect to a virtual box that correlates with a field of view of the ultrasound probe. The processor may be configured to steer the first and second ultrasound signals so that the first and second beam axes are normal with respect to a base of a virtual box that correlates with a field of view of the ultrasound probe.

Certain embodiments of the present disclosure provide a method of steering first and second ultrasound signals transmitted from first and second apertures, respectively, of an ultrasound probe. The method may include transmitting the first ultrasound signal from the first aperture in a first direction that is parallel with a first beam axis of the first ultrasound signal, transmitting the second ultrasound signal from the second aperture in a second direction that is parallel with a second beam axis of the second ultrasound signal, and steering each of the first and second ultrasound signals.

DETAILED DESCRIPTION OF THE DISCLOSURE

Figure 1:
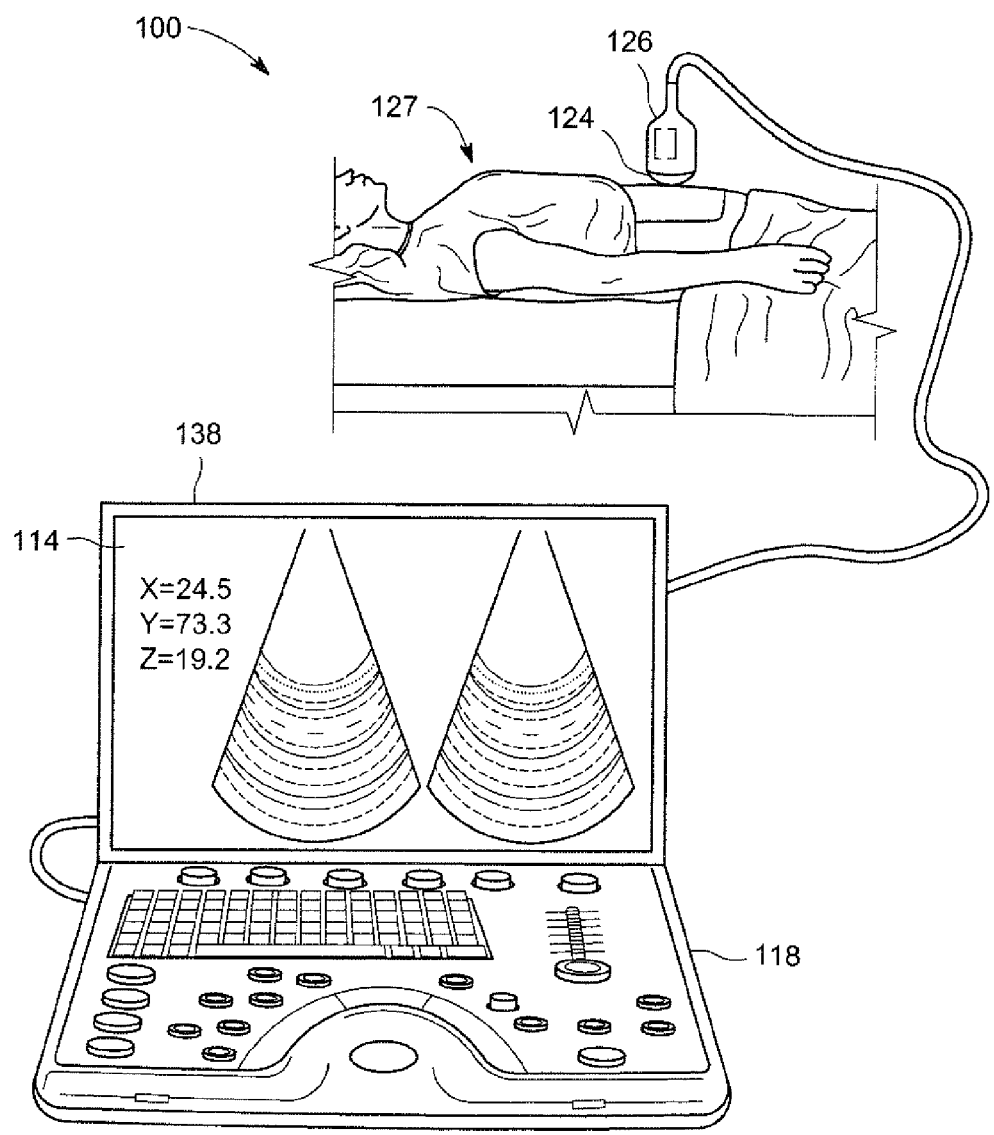
FIG. 1 illustrates an ultrasound imaging system, according to an embodiment of the present disclosure.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry or software. For example, one or more of the functional blocks (for example, processors or memories) may be implemented in a single piece of hardware (for example, a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Further, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Embodiments of the present disclosure provide systems and methods for steering ultrasound signals, such as beams, push pulses, and the like. The ultrasound push pulses may be used to generate shear waves in tissue of a patient. The systems and methods may steer multiple ultrasound signals toward one another to minimize or otherwise reduce any divergence between the ultrasound signals in relation to each other and/or a central longitudinal axis of a transmitting component, such as an array of ultrasound elements, of the probe or transducer. For example, a control unit, which may include one or more processors, of an ultrasound system may simultaneously steer two or more ultrasound signals that are transmitted from a transducer so that beam axes of the ultrasound signals are parallel with each other and/or a central longitudinal axis of the transmitting component. Embodiments of the present disclosure may be used with curved transducers or probes, for example. In at least one other embodiment, linear transducers or probes may be used.

Embodiments of the present disclosure provide systems and methods for simultaneously steering multiple ultrasound signals. For example, a control unit may generate multiple ultrasound signals by generating simultaneous individual phase delay signals for transducer or probe elements. By transmitting the ultrasound signals, such as push pulses, simultaneously, resulting shear waves may simultaneously propagate through patient tissue and be detected by the probe.

Embodiments of the present disclosure provide systems and methods of generating multiple ultrasound push pulses that may generate shear waves of increased magnitude within a defined region of interest. The axes of the push pulses may be steered, such as by the control unit, to be parallel with one another.

Compared to known curved transducer arrays that generate divergent ultrasound signals, embodiments of the present disclosure provide systems and methods that increase shear wave signal strength within a region of interest, thereby leading to better penetration within tissue, and less noise.

FIG. 1 illustrates an ultrasound imaging system 100, according to an embodiment of the present disclosure. The ultrasound imaging system 100 may be configured for shear wave elastography imaging (SWEI). Alternatively, the ultrasound imaging system 100 may be configured for other types of ultrasound imaging, such as strain elastography imaging (SEI). The system 100 may include a workstation 118, such as a portable computer, having a display 138 that is used to show the ultrasound images. Alternatively, the workstation 118 may be a fixed computer system within a location, a handheld device, and/or the like.

In SWEI, ultrasound or ultrasonic signals in the form of push pulses are transmitted into a tissue of a patient. When sufficient energy is transmitted into the tissue, a shear wave is generated within the tissue and propagates outwardly from an origin (the area of tissue into the push pulse(s) are transmitted). The speed of the propagated shear wave depends on the nature of the tissue. For example, a shear wave propagates faster through stiffer tissue. Often, diseased tissue, such as a lesion, is stiffer than healthy tissue. Accordingly, an ultrasound probe that receives shear wave signals may be in communication with a computer or control unit that generates images of the tissue based on the received signals.

An ultrasound system may transmit push pulses into two different areas of patient tissue. By analyzing the speed of the propagating shear waves from each area, the ultrasound system may form images of the patient tissue.

The system 100 may include an ultrasound probe 126 that is coupled to the workstation 118. As the probe 126 acquires measurements of a patient 127, the display 138 may show a region of interest (ROI) data acquisition location 144 illustrated as a three dimensional coordinate. The location 144 represents the location of the probe 126, with respect to the patient 127, when acquiring ultrasound data of the ROI. Alternatively, the location 144 represents the location of the probe 126 with respect to the ROI relative to a reference point, such as a mechanical structure of the ROI, designated by a user (for example, a doctor or operator).

Figure 2:
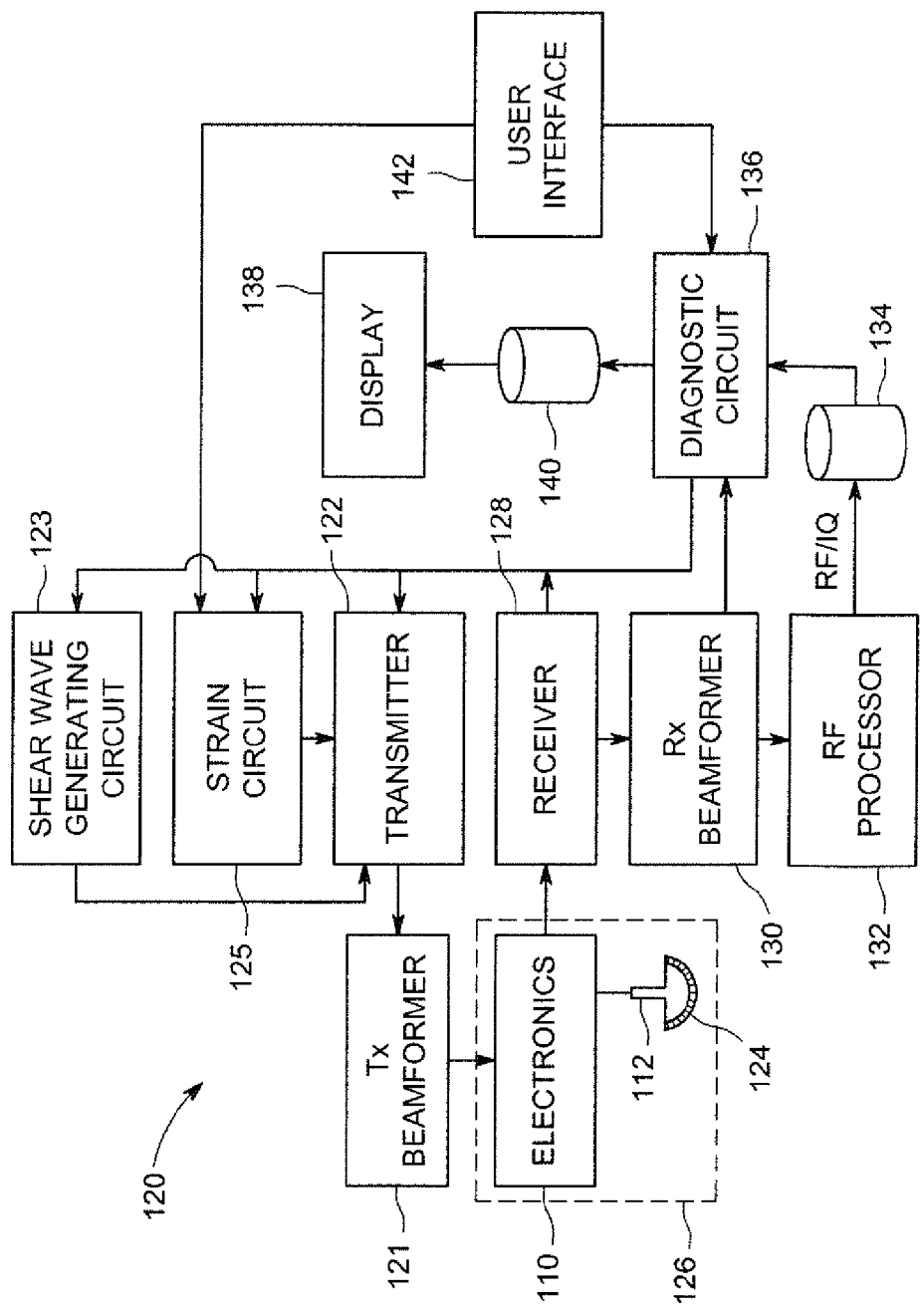
FIG. 2 illustrates a simplified block diagram of an ultrasound imaging system, according to an embodiment of the present disclosure.

FIG. 2 illustrates a simplified block diagram of an ultrasound system 120, according to an embodiment of the present disclosure. The ultrasound system 120 is an example of the ultrasound imaging system 100 shown and described with respect to FIG. 1. In the illustrated embodiment, the ultrasound system 120 may include the probe 126, which may include a transmitter 122 and electronics 110. The transmitter 122 transmits a signal to a transmit beamformer 121 which, in turn, drives transducer elements 124 within a transducer array 112. The transducer elements 124 emit pulsed ultrasonic signals into the patient. As shown in FIG. 2, the array 112 may be a curved array. Alternatively, a variety of other geometries and configurations may be used for the array 112. Further, the array 112 of transducer elements 124 may be provided as part of, for example, different types of ultrasound probes.

The array 112 may include 192 transducer elements 124, for example. Alternatively, more or less transducer elements 124 may be used. Ultrasound beams or pulses may be emitted from apertures formed by groups of transducer elements 124. For example, the array 112 may simultaneously emit two ultrasound signals from two different apertures of 50 transducer elements 124, for example. Optionally, each aperture may be formed by more or less than 50 transducer elements 124. The apertures may or may not overlap.

The transducer elements 124, for example piezoelectric crystals, may emit pulsed ultrasound signals, such as ultrasound push pulses, into a body (for example, a patient) or volume. The ultrasound signals may include, for example, one or more reference pulses, one or more pushing pulses (used to generate shear waves in patient tissue, for example), and/or one or more tracking pulses. At least a portion of the pulsed ultrasound signals back-scatter from a region of interest (ROI) (for example, breast tissues, liver tissues, cardiac tissues, prostate tissues, and the like) to produce echoes. The echoes are delayed in time according to a depth, and are received by the transducer elements 124 within the transducer array 112. The ultrasound signals may be used for imaging, for generating and/or tracking shear waves, for measuring differences in compression displacement of the tissue (for example, strain), and/or for therapy, among other uses. For example, the probe 126 may deliver low energy pulses during imaging and tracking, medium to high energy pulses to generate shear waves, and high energy pulses during therapy.

The transducer array 112 may include a variety of array geometries and configurations for the transducer elements 124 which may be provided as part of, for example, different types of ultrasound probes. The electronics 110 may be used to control the switching of the transducer elements 124. The electronics 110 may also be used to group the transducer elements 124 into one or more apertures or sub-apertures, for example.

The electronics 110 and/or the beamformer 121 may form, or be part of, a control unit that is configured to analyze and steer ultrasound signals. The control unit may be part of a computer, for example. The control unit may be configured to analyze the transmitted directions of the multiple ultrasound signals and steer each of the ultrasound signals. For example, the control unit may include at least one processor that is configured to analyze the directions of transmitted ultrasound signals, in the form of push pulses, and steer each of the ultrasound signals in relation toward or away from each other. For example, the ultrasound signals may be steered toward or away from each other until the ultrasound signals are parallel with one another.

The transducer elements 124 convert the received echo signals into electrical signals which may be received by a receiver 128. The electrical signals representing the received echoes are passed through a receive beamformer 130, which performs beamforming on the received echoes and outputs an RF signal. The RF signal is then provided to an RF processor 132 that processes the RF signal. Alternatively, the RF processor 132 may include a complex demodulator (not shown) that demodulates the RF signal to form IQ data pairs representative of the echo signals. The RF or IQ signal data may then be provided directly to a memory 134 for storage (for example, temporary storage). Optionally, the output of the beamformer 130 may be passed directly to a diagnostic circuit 136.

The ultrasound system 120 may also include a processor or a diagnostic circuit 136 to process the acquired ultrasound information (for example, RF signal data or IQ data pairs) and prepare frames of ultrasound information for display on the display 138. The diagnostic circuit 136 may include one or more separate processing components. For example, the diagnostic circuit 136 may include a central processing unit (CPU), a microprocessor, a graphics processing unit (GPU), or any other electronic component capable of processing inputted data according to specific logical instructions. Having the diagnostic circuit 136 that includes a GPU may be advantageous for computation-intensive operations, such as volume-rendering.

The diagnostic circuit 136 may be adapted to perform one or more processing operations according to a plurality of selectable ultrasound modalities on the acquired ultrasound information. Acquired ultrasound information may be processed in real-time during a scanning or therapy session as the echo signals are received. Additionally or alternatively, the ultrasound information may be stored temporarily in the memory 134 during a scanning session and processed in less than real-time in a live or off-line operation. An image memory 140 is included for storing processed frames of acquired ultrasound information that are not scheduled to be displayed immediately or to store post-processed images (for example, shear wave images, strain images, or the like). The image memory 140 may include any known data storage medium, for example, a permanent storage medium, removable storage medium, or the like.

The diagnostic circuit 136 may be connected to a user interface 142 that controls operation of the diagnostic circuit 136 and the display 138 and may be configured to receive inputs from the user, for example a keyboard, a keypad, buttons, a touchscreen, or the like. The display 138 may include one or more monitors that present patient information, including diagnostic and therapeutic ultrasound images to the user for review, diagnosis, analysis, and treatment. The display 138 may automatically display, for example, one or more 2D, 3D, or 4D ultrasound data sets stored in the memory 134 or 140 or currently being acquired. One or both of the memory 134 and the memory 140 may store 3D data sets of the ultrasound data (for example, shear wave data, strain data, or the like), where such 3D data sets are accessed to present 2D and 3D images. For example, a 3D ultrasound data set may be mapped into the corresponding memory 134 or 140, as well as one or more reference planes. The processing of the data, including the data sets, may be based in part on user inputs, for example, user selections received at the user interface 142.

The diagnostic circuit 136 may be configured to analyze ultrasound signals to obtain the SEI and/or SWEI of the ROI. Furthermore, the diagnostic circuit 136 may also automatically differentiate tissue of the ROI from non-ROI tissue. The diagnostic circuit 136 may also be configured to receive user imaging commands for highlighting or outlining the image, a display layout (for example, side-by-side or overlaid), or otherwise providing an overlay that indicates the ROI within the SEI and/or SWEI.

The diagnostic circuit 136 may be configured to control the probe 126 by having the probe 126 enter into diagnostic or imaging modes such as a shear wave mode or a strain mode. For example, the diagnostic circuit 136 may control the probe 126 to enter the shear wave mode. Once the probe 126 is in the shear wave mode, the probe 126 may be controlled to deliver a pushing pulse to generate a shear wave within the ROI automatically within a predetermined time frame or by the user using the user interface 142.

In operation, the system 120 acquires data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, or the like). The data may be acquired by moving the probe 126, such as along a linear or curvilinear path, while scanning the ROI. At each linear or arcuate position, the probe 126 obtains scan planes that are stored in the memory 134.

The system 120 includes a shear wave-generating circuit 123 that is operatively coupled to the diagnostic circuit 136 or a sub-circuit of the diagnostic circuit 136. The shear wave generating circuit 123 is configured to control the probe 126 when the probe 126 is operated in a shear wave mode. While in the shear wave mode, the shear wave generating circuit 123 may control the probe 126 to generate a shear wave at a site within the ROI of the patient. The shear wave-generating circuit 123 may control the probe 126 or, more particularly, the transducer or probe elements 124 to direct a shear wave-generating or pushing pulse(s) toward the predetermined site to generate the shear wave. Alternatively, the shear wave-generating circuit 123 may control another device capable of generating shear waves having the probe 126 measure or track the velocity as the shear wave passes through the ROI. For example, the shear wave-generating circuit 123 may control a therapy transducer, a mechanical actuator, or an audio device to generate the shear waves.

The system 120 may also include a strain circuit 125 that is operatively coupled to the diagnostic circuit 136 or a sub-circuit of the diagnostic circuit 136. The strain circuit 125 is configured to control the probe 126 when the probe 126 operated in a strain mode. While in the strain mode, the strain circuit 125 may control the probe 126 to generate a mechanical (for example, surface vibration, freehand or step quasi-static surface displacement, or the like) or radiation force on the patient or ROI to measure the stiffness or strain of the ROI of the patient. Alternatively, the strain circuit 125 may control another device capable of generating a mechanical force on the patient or the ROI. For example, a low frequency mechanical vibrator may be applied to the skin surface and the compression motion induced in the underlying tissue, such as on the ROI, is measured by the probe 126.

Figure 3:
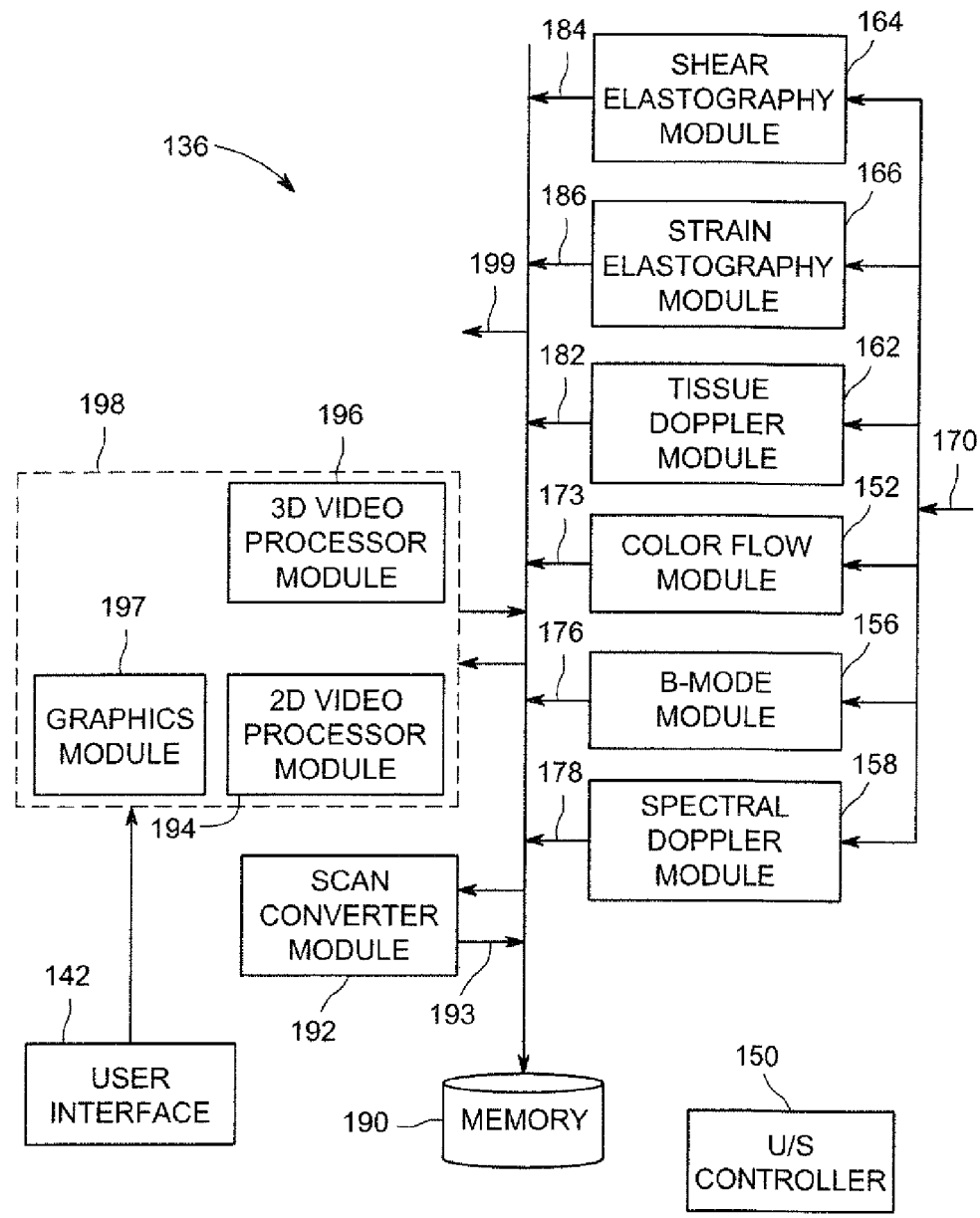
FIG. 3 illustrates a simplified block diagram of a diagnostic circuit of an ultrasound imaging system, according to an embodiment of the present disclosure.

FIG. 3 illustrates an exemplary block diagram of the diagnostic circuit 136, according to an embodiment of the present disclosure. The diagnostic circuit 136 is illustrated conceptually as a collection of circuits, but may be implemented utilizing any combination of dedicated hardware boards, DSPs, processors, etc. Alternatively, the circuit 136 may be implemented utilizing an off-the-shelf PC with a single processor or multiple processors, with the functional operations distributed between the processors. As a further option, the circuit 136 may be implemented utilizing a hybrid configuration in which certain modular functions are performed utilizing dedicated hardware, while the remaining modular functions are performed utilizing an off-the-shelf PC and the like. The circuit 136 also may be implemented as software circuits within a processing unit.

The operations of the circuit 136 may be controlled by a local ultrasound controller 150 or by the diagnostic circuit 136. The circuits 152-166 may perform mid-processor operations. The diagnostic circuit 136 may receive ultrasound data 170 in one of several forms. In the embodiment of FIG. 3, the received ultrasound data 170 constitutes IQ data pairs representing the real and imaginary components associated with each data sample. The IQ data pairs are provided to one or more circuits, for example, a color-flow circuit 152, a B-mode circuit 156, a spectral Doppler circuit 158, a tissue Doppler circuit 162, a shear elastography module or circuit 164, and a strain elastography module or circuit 166. Other circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

Each of circuits 152-166 may be configured to process the IQ data pairs in a corresponding manner to generate, respectively, color-flow data 173, B-mode data 176, spectral Doppler data 178, tissue Doppler data 182, tracking data 184 (for example, ROI data acquisition location), elastography data 186 (for example, strain data, shear wave data), among others, all of which may be stored in a memory 190 (or memory 134 or image memory 140 shown in FIG. 2) temporarily before subsequent processing. The data 173-186 may be stored, for example, as sets of vector data values, where each set defines an individual ultrasound image frame. The vector data values are generally organized based on the polar coordinate system.

A scan converter circuit 192 accesses and obtains from the memory 190 the vector data values associated with an image frame and converts the set of vector data values to Cartesian coordinates to generate an ultrasound image frame 193 formatted for display. The ultrasound image frames 193 generated by the scan converter circuit 192 may be provided back to the memory 190 for subsequent processing or may be provided to the memory 134 (shown in FIG. 2) or the image memory 140 (shown in FIG. 2). Once the scan converter circuit 192 generates the ultrasound image frames 193 associated with the data, the image frames may be stored in the memory 190 or communicated over a bus 199 to a database (not shown), the memory 134, the image memory 140, and/or to other processors (not shown).

For example, it may be desired to view different ultrasound images relating to a shear wave session in real-time on the display 138 (shown in FIGS. 1 and 2). To do so, the scan converter circuit 192 obtains data sets for images stored in the memory 190 of that are currently being acquired from the probe 126 operating in the shear wave mode. The vector data may be interpolated and converted into an X, Y format for video display to produce SWEI image frames. The scan converted SWEI image frames are provided to a display circuit 198 that may include a video processor that maps the video to a gray-scale mapping for video display. The gray-scale map may represent a transfer function of the raw image data to displayed gray levels. Once the video data is mapped to the gray-scale values, the display controller controls the display 138, which may include one or more monitors or windows of the display, to display the SWEI image frame. The SWEI images shown on the display 138 may be produced from an SWEI frame of data in which each datum indicates the intensity or brightness of a respective pixel in the display.

The display circuit 198 accesses and obtains one or more of the image frames from the memory 190 or from the memory 134 and/or the image memory 140 over the bus 199 to display the images onto the display 138. The display circuit 198 receives user input from the user interface 142 selecting one or image frames to be displayed that are stored on memory (for example, the memory 190) and/or selecting a display layout or configuration for the image frames.

The display circuit 198 may include a 2D video processor circuit 194. The 2D video processor circuit 194 may be used to combine one or more of the frames generated from the different types of ultrasound information. For example, the 2D video processor circuit 194 may combine different image frames by mapping one type of data to a gray map and mapping the other type of data to a color map for video display. In the final displayed image, the color pixel data may be superimposed on the gray scale pixel data to form a single multi-mode image frame that is again re-stored in the memory 190 or communicated over the bus 199. Successive frames of images may be stored as a cine loop (4D images) in the memory 190 or memory 140. The cine loop represents a first in, first out circular image buffer to capture image data that is displayed in real-time to the user. The user may freeze the cine loop by entering a freeze command at the user interface 142. The user interface 142 may include, for example, a keyboard and mouse and all other input controls associated with inputting information into the ultrasound system 120 (FIG. 2). In one embodiment, the user interface 142 includes the display 138 that may be touch-sensitive or configured to interact with a stylus. The user interface 142 may also receive user inputs through voice-recognition or activation.

The display circuit 198 may include a 3D processor circuit 196. The 3D processor circuit 196 may access the memory 190 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

The display circuit 198 may include a graphics module or circuit 197. The graphics circuit 197 may access the memory 190 to obtain groups of ultrasound image frames and the ROI data acquisition locations that have been stored or that are currently being acquired. The graphics circuit 197 may generate images that include the images of the ROI and a graphical representation positioned (for example, overlaid) onto the images of the ROI. The graphical representation may represent an outline of a treatment space, the focal point or region of the therapy beam, a path taken by the focal region within the treatment space, a probe used during the session, the ROI data acquisition location, and the like. Graphical representations may also be used to indicate the progress of a therapy session. The graphical representations may be generated using a saved graphical image or drawing (for example, computer graphic generated drawing), or the graphical representation may be directly drawn by the user onto the image using a pointing device, for example, an electronic stylus or mouse, or another interface device.

The systems and circuits shown in FIGS. 1-3 are exemplary. It is to be understood that various other ultrasound systems may be used to generate and analyze ultrasound signals, such as push pulses that are configured to generate shear waves in patient tissue.

Figure 4:
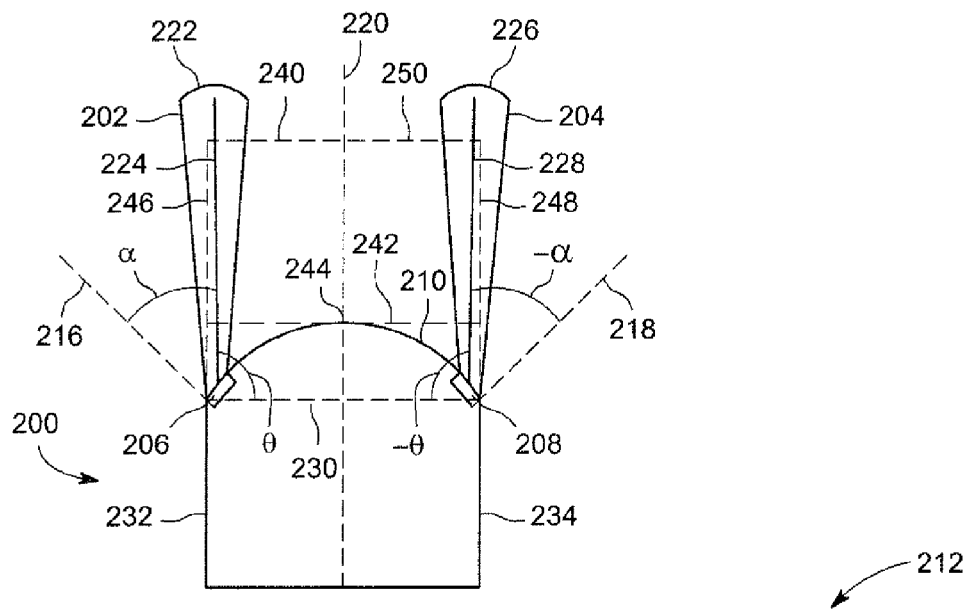
FIG. 4 illustrates a simplified view of an ultrasound probe transmitting ultrasound signals from ultrasound apertures, according to an embodiment of the present disclosure.

FIG. 4 illustrates a simplified view of an ultrasound probe 200 transmitting ultrasound signals 202 and 204 from ultrasound apertures 206 and 208, respectively, according to an embodiment of the present disclosure. The ultrasound signals 202 and 204 may be ultrasound or ultrasonic push pulses that are configured to generate shear waves in patient tissue at two different points. The ultrasound push pulses may be focused or unfocused. Optionally, the ultrasound signals 202 and 204 may be ultrasound push pulses that are configured to generate strain in patient tissue at two different points. Alternatively, the ultrasound signal 202 and 204 may be various other forms of ultrasound or ultrasonic energy other than push pulses.

As shown, the ultrasound probe 200 may be a curved array transducer or probe. The ultrasound probe 200 includes a plurality of ultrasound elements positioned in relation to a front face 210 through which the ultrasound signals 202 and 204 are transmitted. The ultrasound probe 200 may be operated to activate certain ultrasound elements at certain positions to generate the ultrasound signals 202 and 204 from the two different apertures 206 and 208. As shown, the apertures 206 and 208 may be at lateral portions of the face 210 of the probe 200. However, the ultrasound probe 200 may be operated to generate ultrasound signal from apertures at various other positions along the face 210.

Figure 5:
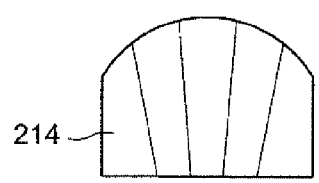
FIG. 5 illustrates a simplified view of an aperture of an ultrasound probe, according to an embodiment of the present disclosure.

FIG. 5 illustrates a simplified view of an aperture 212 of an ultrasound probe, according to an embodiment of the present disclosure. The aperture 212 may be formed by multiple active ultrasound elements 214. As shown, the aperture 212 may be formed by five distinct ultrasound elements 214. It is to be understood that any of the apertures discussed in the present application may be formed through more or less than five ultrasound elements 214. For example, an aperture may be formed by 10, 20, 30, 40, 50, or more ultrasound elements 214.

An ultrasound signal, such as a push pulse, transmitted from the aperture 212 may be steered through phase delay of the individual ultrasound elements 214. For example, the transmit signal for the individual ultrasound elements 214 may be sequentially delayed in order to steer the resulting ultrasound signal in a particular direction.

Referring again to FIG. 4, the ultrasound probe 200 may be a curved probe having the arcuate face 210. Previous curved probes generated ultrasound signals that outwardly diverged from one another. For example, in previous probes, the apertures 206 and 208 transmitted ultrasound signals that were transmitted in diverging directions about axes 216 and 218, respectively. Accordingly, the two locations on the tissue of the patient in which shear waves, for example, were generated were spread apart from one another.

Embodiments of the present disclosure provide the ultrasound probe 200 that may simultaneously transmit and steer the ultrasound signal 202 and the ultrasound signal 204 from the apertures 206 and 208. For example, a control unit (which may include one or more processors) may include the electronics 110 (shown in FIG. 2) and/or the transmit beamformer 121 (shown in FIG. 2), and may simultaneously steer the ultrasound signals 202 and 204, such as push pulses, towards one another. The steered ultrasound signal 202 and 204 may not be normal to the face of the apertures 206 and 208, respectively. Instead, the ultrasound signal 202 may be steered toward a central longitudinal axis 220 of a transmitting component, such as an array of ultrasound elements, of the ultrasound probe 200, while the ultrasound signal 204 may also steered toward the longitudinal axis 220. The longitudinal axis 220 may bisect the ultrasound probe 200. The ultrasound signal 202 and the ultrasound signal 204 may be simultaneously steered toward the longitudinal axis 220. The central longitudinal axis 220 of the transmitting component may or may not be the same or otherwise aligned with the central longitudinal axis of the ultrasound probe 200.

As shown, the central longitudinal axis 220 of the transmitting component is the axis that is aligned with the direction of transmission of each of the ultrasound signals 202 and 204. For example, the central longitudinal axis 220 extends in the same direction as the beam axes 224 and 228. The central longitudinal axis 220 may be parallel with sides 232 and 234 of the ultrasound probe 200.

The ultrasound signal 202 may include a conic beam 222 centered about a central beam axis 224. Similarly, the ultrasound signal 204 may include a conic beam 226 centered about a central beam axis 228. The ultrasound signal 202 may be steered such that the beam axis 224 is at an angle θ with respect to a line 230 that is perpendicular to the central longitudinal axis 220. Similarly, the ultrasound signal 204 may be steered such that the beam axis 228 is at an angle −θ with respect to the line 230. Alternatively, the beams 222 and 226 may not be conic. For example, the beams 222 and 226 may be linear beams that are aligned and parallel with the beam axes 224 and 228, respectively.

The beam axes 224 and 228 may be steered to be parallel with the central longitudinal axis 220. The beam axis 224 may be parallel and aligned with (for example, appearing to emanate from), or inside of, a lateral wall 232 of the ultrasound probe 200. Similarly, the beam axis 228 may be parallel and aligned with, or inside of, a lateral wall 234 of the ultrasound probe 200.

If the ultrasound signals 202 and 204 were not steered toward one another, they would be transmitted normal to the face of the apertures 206 and 208, such that the axes 216 and 218 would represent the beam axes. Accordingly, if the beam 202 were not steered, the beam axes would be at an angle θ+α, while the beam 204 would be at an angle of −θ+−α. Because the beam axes 224 and 228 are steered toward another, however, the ultrasound signals 202 and 204 are steered in converging directions such that the ultrasound signals 202 and 204 may be transmitted in directions that are parallel with the central longitudinal axis 220. As such, the divergence of the ultrasound beams 202 and 204 is eliminated, minimized, or otherwise reduced, and the locations at which each of the ultrasound beams 202 and 204 generate shear waves, for example, on patient tissue are closer (as compared to the un-steered scenario). In this manner, the resulting shear wave energy generated in patient tissue by the ultrasound signals 202 and 204 may be stronger and more reliable.

As shown, the ultrasound signals 202 and 204 may be transmitted such that they are substantially uniform with respect to a virtual box 240 that may correlate with a field of view of the ultrasound probe 200. The ultrasound signals 202 and 204 may be considered to be "substantially uniform" because the ultrasound signals 202 and 204 may naturally flare outwardly the further they travel from the ultrasound probe 200. The box 240 may be formed by a base 242 that is tangent to a point 244 on the face 210 of the probe 200 that is at the central longitudinal axis 220. Sides 246 and 248 of the box 240 extend from the sides 232 and 234, respectively, of the ultrasound probe 200, and are parallel with the central longitudinal axis 220. An end line 250 of the box 240 is parallel with the base 244 and may be a distance from the base 244 that corresponds to a portion, such as an end or an operator-defined end, of a field of view. Because the ultrasound signals 202 and 204 are steered toward one another such that the beam axes 224 and 228, respectively, are parallel with the central longitudinal axis 220, the strength of each ultrasound signal 202 and 204 at the end line 250 may be the same, or substantially the same, as at the base 242. In contrast, if the beams 202 and 204 were not steered toward another, the beams 202 and 204 would diverge away from one another such that the energies proximate to the end line 250 may be attenuated and weaker.

As shown in FIG. 4, the ultrasound signals 202 and 204 may be transmitted so that they are normal to the base 242 of the virtual box 240, instead of being transmitted so that they are normal to the face of each aperture 206 and 208, respectively. Therefore, the ultrasound signals 202 and 204 may be transmitted in a parallel fashion with respect to a curved ultrasound probe, for example, as opposed to diverging from one another. Embodiments of the present disclosure may be used to simultaneously steer multiple independent ultrasound signals, such as the ultrasound signals 202 and 204, along a parallel trajectory.

By steering the ultrasound signals 202 and 204 toward one another or otherwise toward the central longitudinal axis 220 (such as with respect to a common direction), the signal strengths of the ultrasound beams 202 and 204 remains stable. As noted, the ultrasound signals 202 and 204 may be push pulses that are configured to generate shear waves in patient tissue. Alternatively, the ultrasound signals 202 and 204 may be various other ultrasound signals.

As shown in FIG. 4, two ultrasound beams 202 and 204 may be transmitted from two apertures 206 and 208, respectively. Optionally, more or less ultrasound beams may be generated from more or less apertures. For example, the ultrasound probe 200 may transmit one of the ultrasound signals 202 or 204 from the apertures 206 or 208, and steer that beam toward the longitudinal axis 220 such that the beam axis 224 or 228 is parallel with the central longitudinal axis 220. As another example, additional ultrasound signals may be generated and simultaneously steered along with the ultrasound signals 202 and 204.

As described above, the ultrasound signals 202 and 204 may be steered toward one another such that the beam axes 224 and 228 are parallel with the central longitudinal axis 220. Alternatively, the beams 202 and 204 may be steered so that the beam axes 224 and 228 are not parallel with the central longitudinal axis 220. For example, the ultrasound signals 202 and 204 may be steered toward another such that they converge to a focal point of a field of view, for example, of the ultrasound probe 200. In at least one embodiment, the ultrasound signals 202 and 204 may be steered toward one another so that they intersect. For example, the ultrasound signals 202 and 204 may be push pulses that constructively interfere to generate a higher energy shear wave at a single point of patient tissue. The higher energy shear wave may have an increased signal-to-noise ratio, for example. In at least one other embodiment, the ultrasound signals may be steered toward each other such that they intersect at a single point to deliver therapy to patient tissue.

Figure 6:
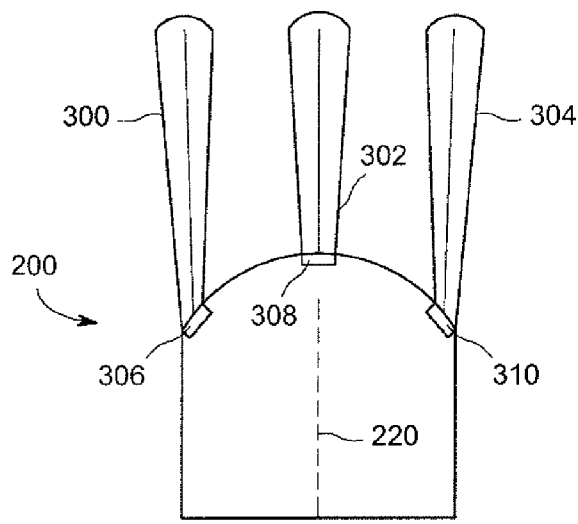
FIG. 6 illustrates a simplified view of an ultrasound probe transmitting ultrasound signals from ultrasound apertures, according to an embodiment of the present disclosure.

FIG. 6 illustrates a simplified view of the ultrasound probe 200 transmitting ultrasound signals 300, 302, and 304 from ultrasound apertures 306, 308, and 310, respectively, according to an embodiment of the present disclosure. As shown, the three ultrasound signals 300, 302, and 304, such as ultrasound push pulses configured to generate shear waves in tissue, may be transmitted from the ultrasound probe 200. Each signal 300, 302, and 304 may be transmitted such that the beam axes are parallel with the central longitudinal axis 220. As such, the signals 300 and 304 may be steered toward the central longitudinal axis 220, while the signal 302 may be transmitted and un-steered, as it may naturally be aligned with respect to the central longitudinal axis 220.

Figure 7:
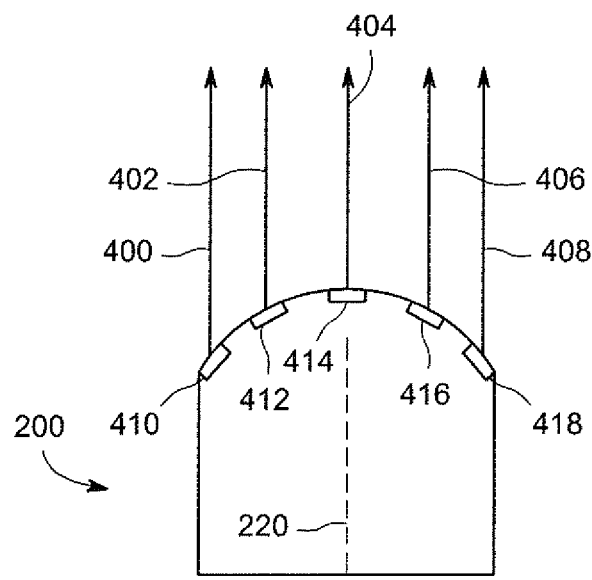
FIG. 7 illustrates a simplified view of an ultrasound probe transmitting ultrasound signals from ultrasound apertures, according to an embodiment of the present disclosure.

FIG. 7 illustrates a simplified view of the ultrasound probe 200 transmitting ultrasound signals 400, 402, 404, 406, and 408 from ultrasound apertures 410, 412, 414, 416, and 418, respectively, according to an embodiment of the present disclosure. For the sake of clarity, the ultrasound signals are represented by beam axes. As shown, the ultrasound probe 200 may transmit five separate ultrasound signals 400-408 from five separate apertures 410-418. If not already parallel with the central longitudinal axis 220, the ultrasound signals 400-408 may be steered, such as through a control unit, towards one another, such as to be parallel with the central longitudinal axis 220.

Figure 8:
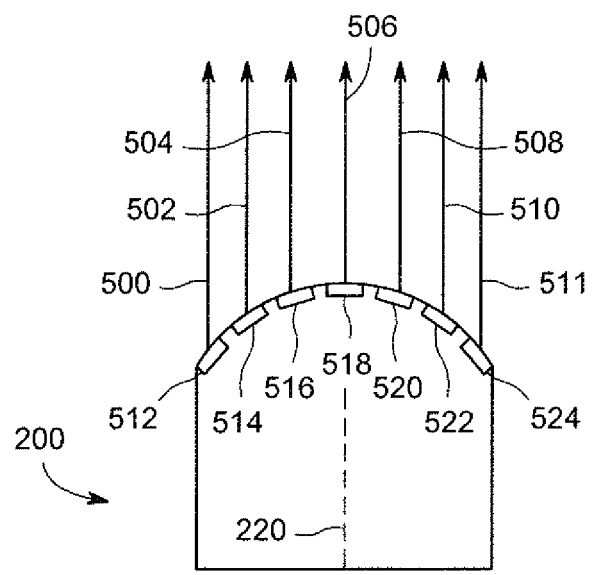
FIG. 8 illustrates a simplified view of an ultrasound probe transmitting ultrasound signals from ultrasound apertures, according to an embodiment of the present disclosure.

FIG. 8 illustrates a simplified view of the ultrasound probe 200 transmitting ultrasound signals 500, 502, 504, 506, 508, 510, and 511 from ultrasound apertures 512, 514, 516, 518,

520, 522, and 524, respectively, according to an embodiment of the present disclosure. For the sake of clarity, the ultrasound signals are represented by beam axes. As shown, the ultrasound probe 200 may transmit seven separate ultrasound signals 500-511 from seven separate apertures 512-524. If not already parallel with the central longitudinal axis 220, the ultrasound signals 500-511 may be steered, such as through a control unit, towards one another, such as to be parallel with the central longitudinal axis 220.

Referring to FIGS. 4-8, the ultrasound probe 200 may transmit more or less ultrasound signals than shown and described. Further, each aperture may be formed from one or more ultrasound elements.

Figure 9:
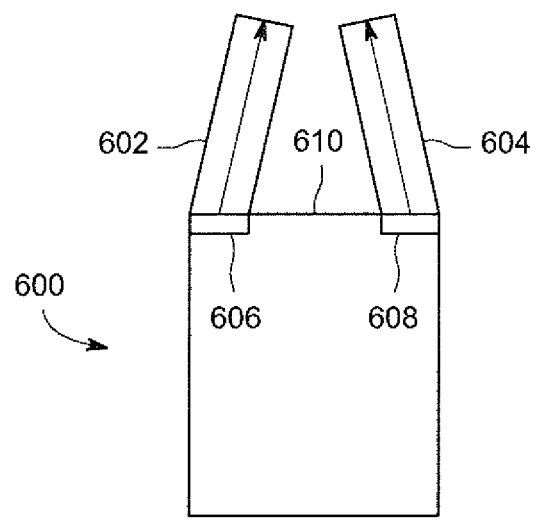
FIG. 9 illustrates a simplified view of an ultrasound probe transmitting ultrasound signals from ultrasound apertures, according to an embodiment of the present disclosure.

FIG. 9 illustrates a simplified view of an ultrasound probe 600 transmitting ultrasound signals 602 and 604 from ultrasound apertures 606 and 608, respectively, according to an embodiment of the present disclosure. The ultrasound probe 600 may be a linear probe having a straight face 610. Embodiments of the present disclosure may be used with various ultrasound probes, whether curved, linear, or the like.

Figure 10:
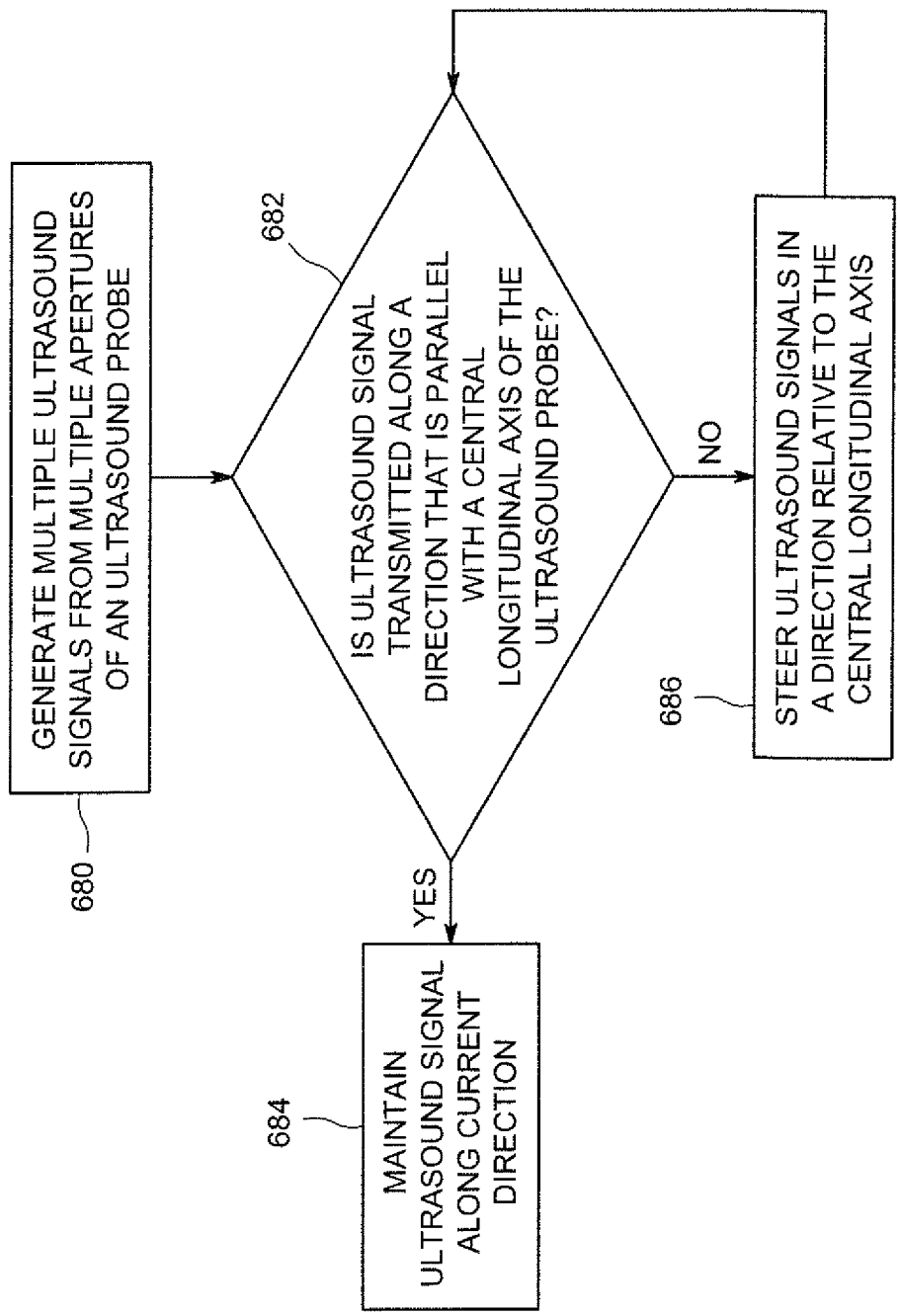
FIG. 10 illustrates a flow chart of a method of transmitting multiple ultrasound signals from a single ultrasound probe, according to an embodiment of the present disclosure.

FIG. 10 illustrates a flow chart of a method of transmitting multiple ultrasound signals from a single ultrasound probe, according to an embodiment of the present disclosure. At 680, multiple ultrasound signals are generated from multiple apertures of an ultrasound probe. The ultrasound signals may be push pulses that are configured to generate shear waves originating from two origins on patient tissue. The ultrasound signals may be simultaneously generated.

Next, at 682, it is determined whether each ultrasound signal is transmitted along a direction that is parallel with a central longitudinal axis of a transmitting component of the ultrasound probe. For example, a computer, a control unit, one or more processors, and/or the like may analyze the ultrasound signals to determine their directions in relation to the central longitudinal axis. If an ultrasound signal is parallel with the central longitudinal axis, the ultrasound signal is maintained along its current direction at 684. If, however, the direction of transmission of the ultrasound signal is not parallel to the central longitudinal axis, the ultrasound signal is steered in a direction relative to the central longitudinal axis at 686. For example, the ultrasound signal may be steered toward or away from the central longitudinal axis. The method then returns to 682.

As described above, embodiments of the present disclosure provide systems and methods for steering ultrasound signals. The ultrasound signals may be used to generate shear waves in tissue of a patient. For example, a control unit or at least one processor may steer multiple ultrasound signals toward one another to eliminate, minimize, or otherwise reduce any divergence between the ultrasound signals in relation to a central longitudinal axis of a transmitting component of the probe or transducer.

Embodiments of the present disclosure provide systems and methods for generating multiple ultrasound push pulses that may generate shear waves of increased magnitude within a defined region of interest. The push pulses may be steered, such as by the control unit and/or at least one processor, to be parallel with one another.

Compared to known curved transducer arrays that generate divergent beams, embodiments of the present disclosure provide systems and methods that increase shear wave signal strength within a region of interest, thereby leading to better penetration within tissue, and less noise.

Figure 11:
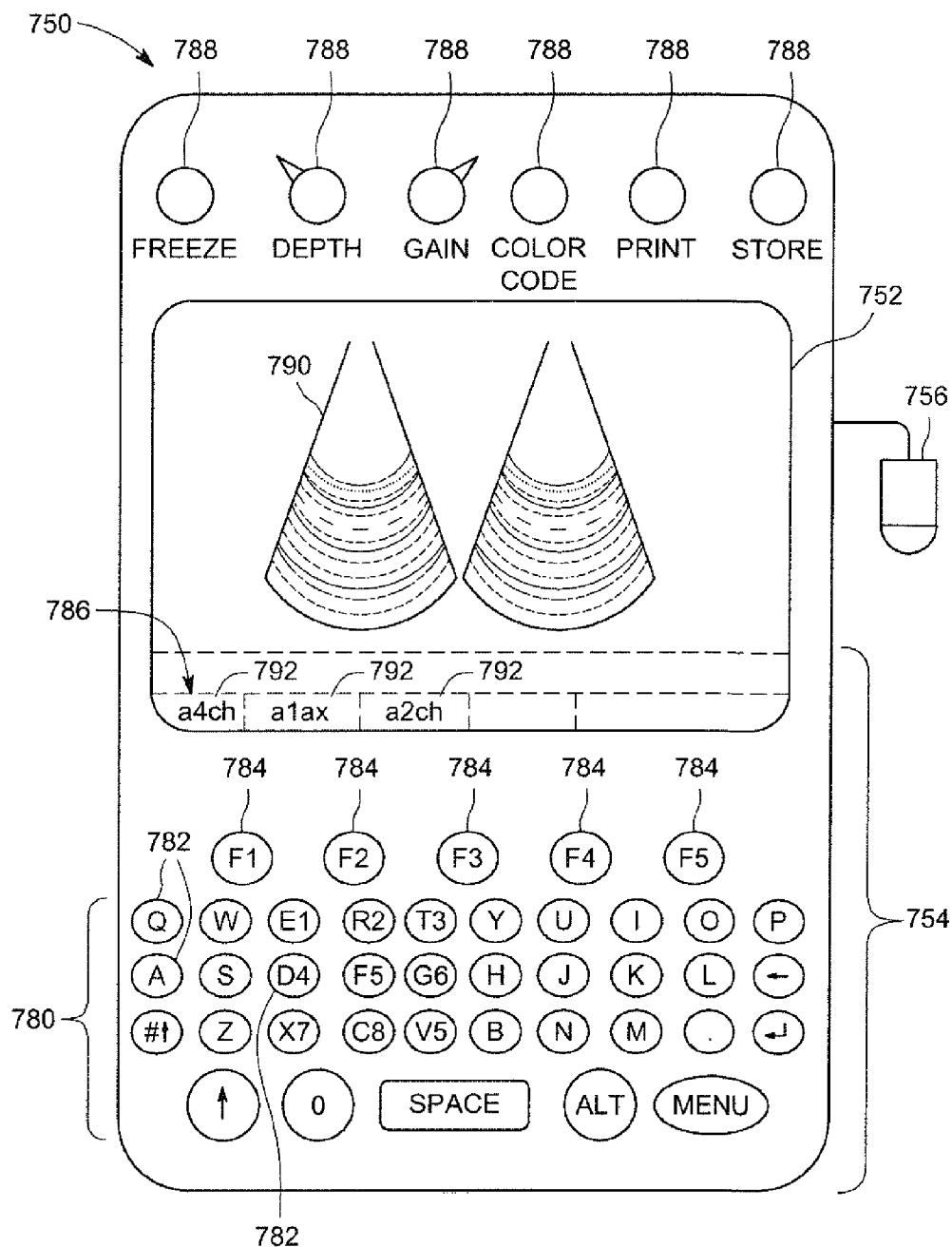
FIG. 11 illustrates a hand carried or pocket-sized ultrasound imaging system, according to an embodiment of the present disclosure.

FIG. 11 illustrates a hand carried or pocket-sized ultrasound imaging system 750 in which a display 752 and user interface 754 form a single unit, according to an embodiment of the present disclosure. By way of example, the pocket-sized ultrasound imaging system 750 may be a pocket-sized or hand-sized ultrasound system approximately 2 inches wide, approximately 4 inches in length, and approximately 0.5 inches in depth and weighs less than 3 ounces. The pocket-sized ultrasound imaging system 750 generally includes the display 752, user interface 754, which may or may not include a keyboard-type interface and an input/output (I/O) port for connection to a scanning device, for example, an ultrasound probe 756, such as any of those described above. The display 752 may be, for example, a 320×320 pixel color LCD display (on which a medical image 790 may be displayed). A typewriter-like keyboard 780 of buttons 782 may optionally be included in the user interface 754.

Multi-function controls 784 may each be assigned functions in accordance with the mode of system operation (for example, displaying different views). Therefore, each of the multi-function controls 784 may be configured to provide a plurality of different actions. Label display areas 786 associated with the multi-function controls 784 may be included as necessary on the display 752. The system 750 may also have additional keys and/or controls 788 for special purpose functions, which may include, but are not limited to "freeze," "depth control," "gain control," "color-mode," "print," and "store."

One or more of the label display areas 786 may include labels 792 to indicate the view being displayed or allow a user to select a different view of the imaged object to display. The selection of different views also may be provided through the associated multi-function control 784. The display 752 may also have a textual display area 794 for displaying information relating to the displayed image view (for example, a label associated with the displayed image).

It should be noted that the various embodiments of the present disclosure may be implemented in connection with miniaturized or small-sized ultrasound systems having different dimensions, weights, and power consumption. For example, the pocket-sized ultrasound imaging system 750 and the miniaturized ultrasound system 930 (shown in FIG. 13) may provide the same scanning and processing functionality as the system 100.

Figure 12:
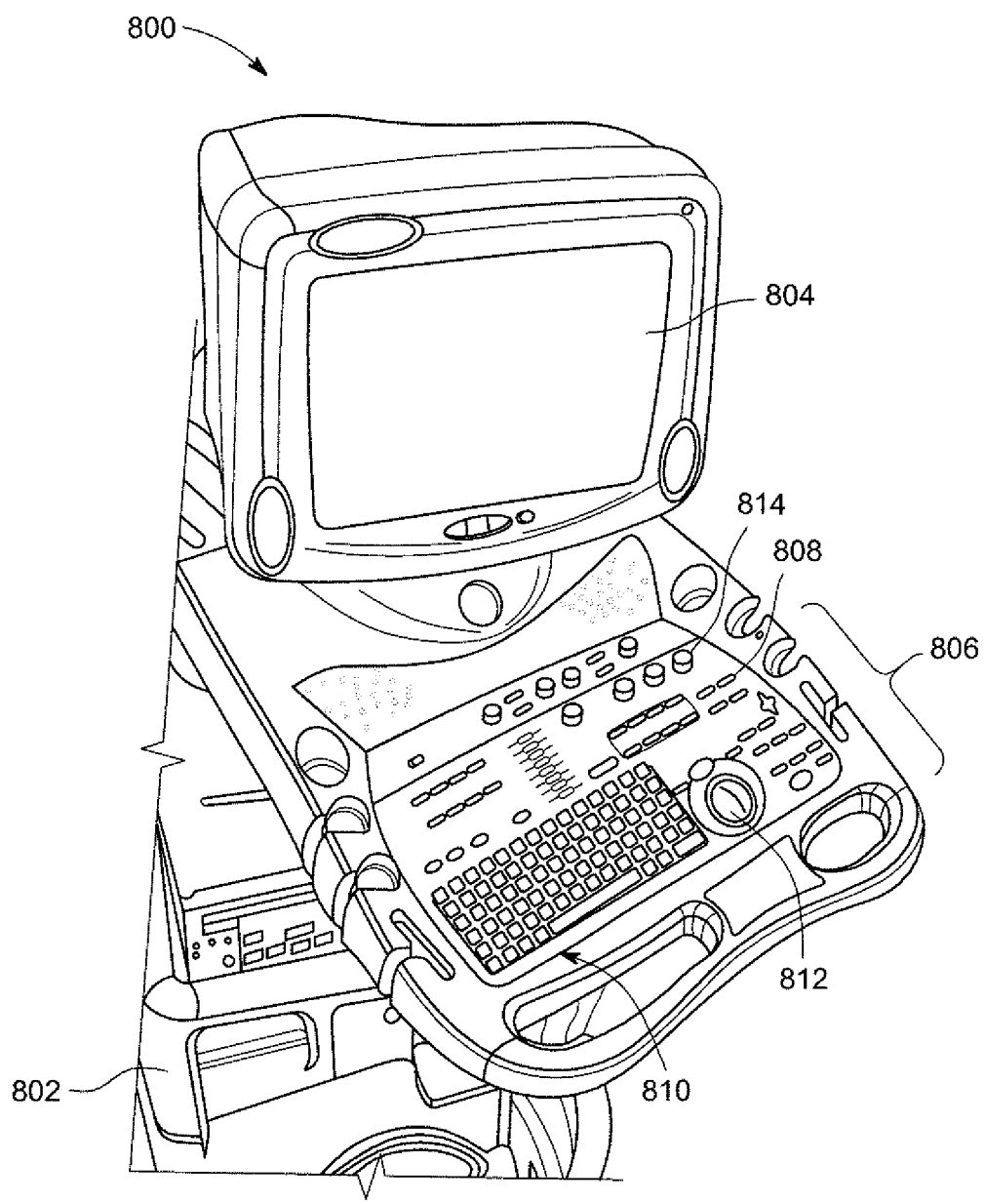
FIG. 12 illustrates a console-based ultrasound imaging system, according to an embodiment of the present disclosure.

FIG. 12 illustrates an ultrasound imaging system 800 provided on a movable base 802, according to an embodiment of the present disclosure. The portable ultrasound imaging system 800 may also be referred to as a cart-based system. A display 804 and user interface 806 are provided and it should be understood that the display 804 may be separate or separable from the user interface 806. The user interface 806 may optionally be a touchscreen, allowing the operator to select options by touching displayed graphics, icons, and the like.

The user interface 806 also includes control buttons 808 that may be used to control the portable ultrasound imaging system 800 as desired or needed, and/or as typically provided. The user interface 806 provides multiple interface options that the user may physically manipulate to interact with ultrasound data and other data that may be displayed, as well as to input information and set and change scanning parameters and viewing angles, etc. For example, a keyboard 810, trackball 812 and/or multi-function controls 814 may be provided.

Figure 13:
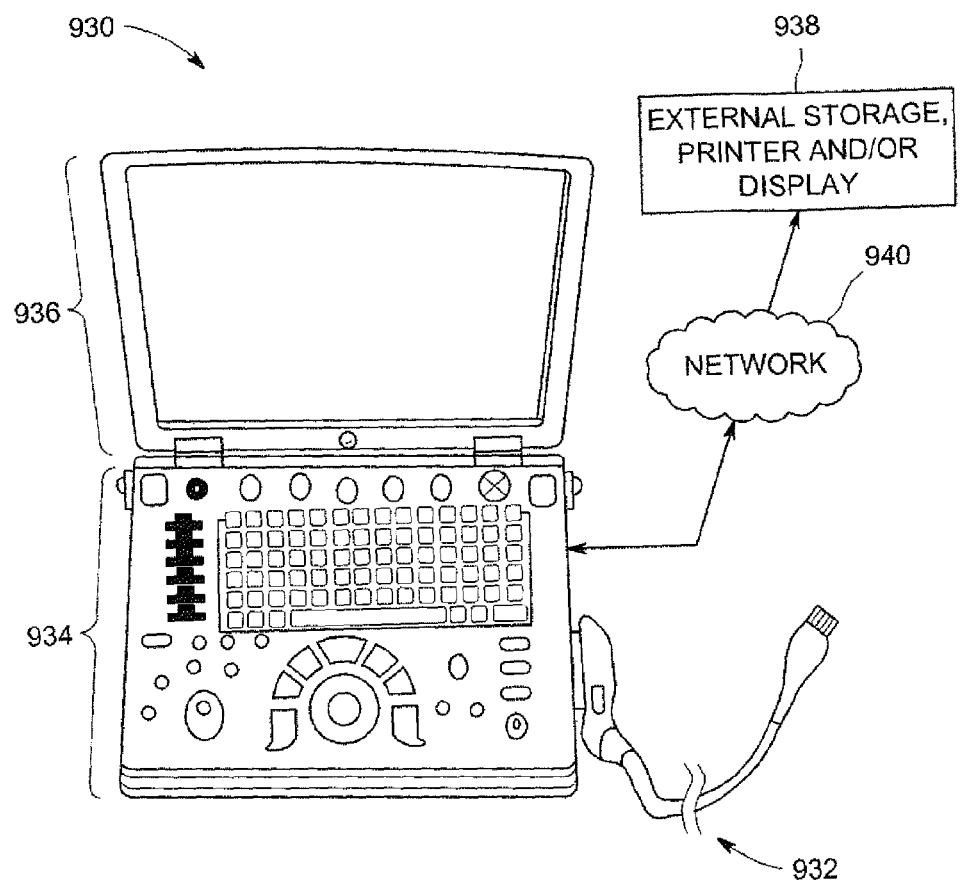
FIG. 13 illustrates a miniaturized ultrasound imaging system, according to an embodiment of the present disclosure.

FIG. 13 illustrates a 3D-capable miniaturized ultrasound system 930 having a probe 932 that may be configured to acquire 3D ultrasonic data or multi-plane ultrasonic data, according to an embodiment of the present disclosure. For example, the probe 932 may have a 2D array of elements. A user interface 934 (that may also include an integrated display 936) is provided to receive commands from an operator. As used herein, "miniaturized" means that the ultrasound system 930 is a handheld or hand-carried device or is configured to be carried in a person's hand, pocket, briefcase-sized case, or backpack. For example, the ultrasound system 930 may be a hand-carried device having a size of a typical laptop computer. The ultrasound system 930 is easily portable by the operator. The integrated display 936 (for example, an internal display) is configured to display, for example, one or more medical images.

The ultrasonic data may be sent to an external device 938 via a wired or wireless network 940 (or direct connection, for example, via a serial or parallel cable or USB port). In some embodiments, the external device 938 may be a computer or a workstation having a display. Alternatively, the external device 938 may be a separate external display or a printer capable of receiving image data from the hand carried ultrasound system 930 and of displaying or printing images that may have greater resolution than the integrated display 936.

It should be noted that the various embodiments may be implemented in hardware, software or a combination thereof. The various embodiments and/or components, for example, the circuits, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "circuit" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or circuits, a program circuit within a larger program or a portion of a program circuit. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, any use of the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An ultrasound system, comprising:
a curved probe including a first set of elements that define a first aperture, and a second set of elements that define a second aperture, wherein the probe is configured to transmit first and second ultrasound signals from the first and second apertures, respectively, wherein the first and second ultrasound signals are first and second push pulses configured to generate shear waves in tissue, wherein the first ultrasound signal is configured to be transmitted in a first direction that is parallel with a first beam axis of the first ultrasound signal, and wherein the second ultrasound signal is separate and distinct from the first ultrasound signal and configured to be transmitted in a second direction that is parallel with a second beam axis of the second ultrasound signal; and
at least one processor that is configured to independently steer each of the first and second ultrasound signals.

2. The ultrasound system of claim 1, wherein the at least one processor is configured to steer each of the first and second ultrasound signals in relation to a central longitudinal axis of a transmitting component of the probe.

3. The ultrasound system of claim 2, wherein the at least one processor is configured to steer each of the first and second ultrasound signals so that the first and second beam axes are parallel with the central longitudinal axis.

4. The ultrasound system of claim 1, wherein the first direction is not normal to a first face of the first aperture, and wherein the second direction is not normal to a second face of the second aperture.

5. The ultrasound system of claim 1, wherein the at least one processor is configured to steer the first and second ultrasound signals with respect to one another so that the first and second beam axes are parallel.

6. The ultrasound system of claim 1, wherein the at least one processor is configured to steer the first and second ultrasound signals to be substantially uniform with respect to a virtual box that correlates with a field of view of the ultrasound probe.

7. The ultrasound system of claim 1, wherein the at least one processor is configured to steer the first and second ultrasound signals so that the first and second beam axes are normal with respect to a base of a virtual box that correlates with a field of view of the ultrasound probe.

8. The ultrasound system of claim 1, wherein the at least one processor is configured to steer the first and second ultrasound signals towards one another.

9. The ultrasound system of claim 1, wherein the probe is configured to simultaneously transmit the first and second ultrasound signals from the first and second apertures, respectively.

10. A method of steering separate and distinct first and second ultrasound signals transmitted from first and second apertures, respectively, of an ultrasound probe, wherein the first and second ultrasound signals are first and second push pulses configured to generate shear waves in tissue, the method comprising:
transmitting the first ultrasound signal from the first aperture in a first direction that is parallel with a first beam axis of the first ultrasound signal;
transmitting the second ultrasound signal from the second aperture in a second direction that is parallel with a second beam axis of the second ultrasound signal; and
steering each of the first and second ultrasound signals.

11. The method of claim 10, wherein the steering operation comprises steering each of the first and second ultrasound signals in relation to a central longitudinal axis of a transmitting component the probe.

12. The method of claim 11, wherein the steering operation further comprises steering each of the first and second ultrasound signals so that the first and second beam axes are parallel with one another and the central longitudinal axis.

13. The method of claim 10, wherein the steering operation comprises steering the first and second ultrasound signals to be substantially uniform with respect to a virtual box that correlates with a field of view of the ultrasound probe.

14. The method of claim 10, wherein the steering operation comprises steering the first and second ultrasound signals so that the first and second beam axes are normal with respect to a base of virtual box that correlates with a field of view of the ultrasound probe.

15. The method of claim 10, wherein the steering operation comprises steering the first and second ultrasound signals towards one another.

16. The method of claim 10, wherein the probe is a curved ultrasound probe.

17. An ultrasound system, comprising:
a curved probe including a transmitting component having a central longitudinal axis and including a plurality of sets of elements that define a plurality of apertures, wherein the probe is configured to simultaneously transmit a plurality of ultrasound push pulses from the plurality of apertures, wherein each of the plurality of ultrasound push pulses is configured to generate at least one shear wave in patient tissue, wherein each of the plurality of ultrasound push pulses is configured to be transmitted in a direction that is parallel with a beam axis of each the plurality of ultrasound push pulses; and
at least one processor that is configured to independently steer each of the plurality of ultrasound push pulses toward each other to be parallel with the central longitudinal axis, wherein the at least one processor is configured to steer each of the plurality of ultrasound push pulses to be substantially uniform with respect to a virtual box that correlates with a field of view of the ultrasound probe, wherein the at least one processor is configured to steer each of the plurality of ultrasound push pulses so that the beam axes of the plurality of ultrasound push pulses are normal with respect to a base of the virtual box.

18. An ultrasound system, comprising:
a curved probe including a first set of elements that define a first aperture, and a second set of elements that define a second aperture, wherein the probe is configured to transmit first and second ultrasound signals from the first and second apertures, respectively, wherein the first ultrasound signal is configured to be transmitted in a first direction that is parallel with a first beam axis of the first ultrasound signal, and wherein the second ultrasound signal is separate and distinct from the first ultrasound signal and configured to be transmitted in a second direction that is parallel with a second beam axis of the second ultrasound signal; and
at least one processor that is configured to independently steer each of the first and second ultrasound signals, wherein the at least one processor is configured to steer the first and second ultrasound signals to be substantially uniform with respect to a virtual box that correlates with a field of view of the ultrasound probe.

19. The ultrasound system of claim 18, wherein the at least one processor is configured to steer each of the first and second ultrasound signals in relation to a central longitudinal axis of a transmitting component of the probe.

20. The ultrasound system of claim 19, wherein the at least one processor is configured to steer each of the first and second ultrasound signals so that the first and second beam axes are parallel with the central longitudinal axis.

21. The ultrasound system of claim 18, wherein the first direction is not normal to a first face of the first aperture, and wherein the second direction is not normal to a second face of the second aperture.

22. The ultrasound system of claim 18, wherein the at least one processor is configured to steer the first and second ultrasound signals with respect to one another so that the first and second beam axes are parallel.

23. The ultrasound system of claim 18, wherein the at least one processor is configured to steer the first and second ultrasound signals towards one another.

24. The ultrasound system of claim 18, wherein the probe is configured to simultaneously transmit the first and second ultrasound signals from the first and second apertures, respectively.

25. An ultrasound system, comprising:
a curved probe including a first set of elements that define a first aperture, and a second set of elements that define a second aperture, wherein the probe is configured to transmit first and second ultrasound signals from the first and second apertures, respectively, wherein the first ultrasound signal is configured to be transmitted in a first direction that is parallel with a first beam axis of the first ultrasound signal, and wherein the second ultrasound signal is separate and distinct from the first ultrasound signal and configured to be transmitted in a second direction that is parallel with a second beam axis of the second ultrasound signal; and
at least one processor that is configured to independently steer each of the first and second ultrasound signals, wherein the at least one processor is configured to steer the first and second ultrasound signals so that the first and second beam axes are normal with respect to a base of a virtual box that correlates with a field of view of the ultrasound probe.

26. The ultrasound system of claim 25, wherein the at least one processor is configured to steer each of the first and second ultrasound signals in relation to a central longitudinal axis of a transmitting component of the probe.

27. The ultrasound system of claim 26, wherein the at least one processor is configured to steer each of the first and second ultrasound signals so that the first and second beam axes are parallel with the central longitudinal axis.

28. The ultrasound system of claim 25, wherein the first direction is not normal to a first face of the first aperture, and wherein the second direction is not normal to a second face of the second aperture.

29. The ultrasound system of claim 25, wherein the at least one processor is configured to steer the first and second ultrasound signals with respect to one another so that the first and second beam axes are parallel.

30. The ultrasound system of claim 25, wherein the at least one processor is configured to steer the first and second ultrasound signals towards one another.

31. The ultrasound system of claim 25, wherein the probe is configured to simultaneously transmit the first and second ultrasound signals from the first and second apertures, respectively.

32. A method of steering separate and distinct first and second ultrasound signals transmitted from first and second apertures, respectively, of an ultrasound probe, the method comprising:
transmitting the first ultrasound signal from the first aperture in a first direction that is parallel with a first beam axis of the first ultrasound signal;
transmitting the second ultrasound signal from the second aperture in a second direction that is parallel with a second beam axis of the second ultrasound signal; and
steering each of the first and second ultrasound signals, wherein the steering operation comprises steering the first and second ultrasound signals to be substantially uniform with respect to a virtual box that correlates with a field of view of the ultrasound probe.

33. The method of claim 32, wherein the steering operation comprises steering each of the first and second ultrasound signals in relation to a central longitudinal axis of a transmitting component the probe.

34. The method of claim 33, wherein the steering operation further comprises steering each of the first and second ultrasound signals so that the first and second beam axes are parallel with one another and the central longitudinal axis.

35. The method of claim 32, wherein the steering operation comprises steering the first and second ultrasound signals towards one another.

36. The method of claim 32, wherein the probe is a curved ultrasound probe.

37. A method of steering separate and distinct first and second ultrasound signals transmitted from first and second apertures, respectively, of an ultrasound probe, the method comprising:
transmitting the first ultrasound signal from the first aperture in a first direction that is parallel with a first beam axis of the first ultrasound signal;
transmitting the second ultrasound signal from the second aperture in a second direction that is parallel with a second beam axis of the second ultrasound signal; and
steering each of the first and second ultrasound signals, wherein the steering operation comprises steering the first and second ultrasound signals so that the first and second beam axes are normal with respect to a base of virtual box that correlates with a field of view of the ultrasound probe.

38. The method of claim 37, wherein the steering operation comprises steering each of the first and second ultrasound signals in relation to a central longitudinal axis of a transmitting component the probe.

39. The method of claim 38, wherein the steering operation further comprises steering each of the first and second ultrasound signals so that the first and second beam axes are parallel with one another and the central longitudinal axis.

40. The method of claim 37, wherein the steering operation comprises steering the first and second ultrasound signals towards one another.

41. The method of claim 37, wherein the probe is a curved ultrasound probe.

* * * * *